US 6,706,921 B2

(12) United States Patent
Bartmann et al.

(10) Patent No.: US 6,706,921 B2
(45) Date of Patent: Mar. 16, 2004

(54) METHOD FOR PRODUCING SULFONYL-BENZOYL GUANIDINIUM SALTS

(75) Inventors: Ekkehard Bartmann, Erzhausen (DE); Michael Kirschbaum, Weiterstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/275,484

(22) PCT Filed: Apr. 17, 2001

(86) PCT No.: PCT/EP01/04294

§ 371 (c)(1),
(2), (4) Date: Nov. 6, 2002

(87) PCT Pub. No.: WO01/85679

PCT Pub. Date: Nov. 15, 2001

(65) Prior Publication Data

US 2003/0162999 A1 Aug. 28, 2003

(30) Foreign Application Priority Data

Dec. 5, 2000  (DE) .......................... 100 23 405

(51) Int. Cl.$^7$ ............................. C07C 233/05
(52) U.S. Cl. ..................................... 564/162
(58) Field of Search ......................... 564/162

(56) References Cited

U.S. PATENT DOCUMENTS 5,591,754 A * 1/1997 Lang et al. .................. 514/331
5,744,641 A    4/1998 Gericke et al.

FOREIGN PATENT DOCUMENTS

EP  0758644  2/1997

OTHER PUBLICATIONS

A.Ulman et al., "Novel synthesis of 4–'alky(aryl)sulphonyl benzaldehydes: alkyl(aryl)sulphinate anion as a nucleophile in aromatic substitutions," Journal of Organic Chemistry, Sep. 15, 1989, pp. 4691–4692.

M.Baumgarth et al., "(2–Methyl–5–(methylsulphonyl)benzoyl)–guanidine Na+/H+ antiporter inhibitors," Journal of Medicinal Chemistry, Jun. 20, 1997, pp. 2017–2034.

* cited by examiner

Primary Examiner—Shailendra Kumar
(74) Attorney, Agent, or Firm—Millen, White, Zelano & Branigan, P.C.

(57) ABSTRACT

The invention relates to a method for producing acid addition salts of compounds of formula (I), wherein $R^1$, $R^2$ and $R^3$ represent alkyl with 1 to 12 C-atoms.

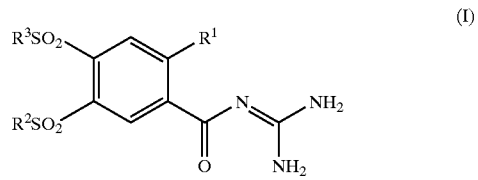

(I)

17 Claims, No Drawings

METHOD FOR PRODUCING SULFONYL-BENZOYL GUANIDINIUM SALTS

This application is a 371 of PCT/EP01/04294, filed Apr. 17, 2001.

The invention relates to a process for the preparation of acid-addition salts of the compounds of the formula I

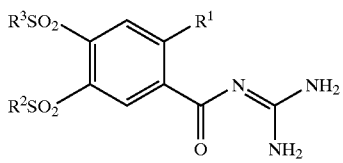

in which $R^1$, $R^2$ and $R^3$, independently of one another, are alkyl having from 1 to 12 carbon atoms, characterised in that, in a step A, the compounds of the formula II

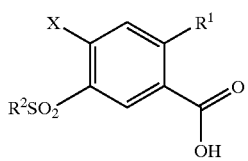

in which $R^1$ and $R^2$ are as defined above, and X is F, Cl, Br, alkyl- or arylsulfonate or perfluoroalkylsulfonate, are converted by conventional methods into the esters of the formula III

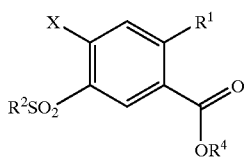

in which $R^1$, $R^2$ and X are as defined above, and $R^4$ is alkyl having from 1 to 10 carbon atoms, and, in a step B, these are converted in the presence of alkylsulfinate into the compounds of the formula IV

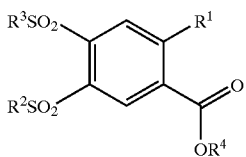

in which $R^1$, $R^2$, $R^3$ and $R^4$ are as defined above, the resultant compounds of the formula IV are, in a step C, converted by reaction with guanidine into the corresponding compounds of the formula I, and, in a step D, these are treated with a suitable acid in order to form the acid-addition salt.

Sulfonylbenzoylguanidines are known and are described, for example, in EP 0 758 644 A1. These substances are inhibitors of the cellular $Na^+/H^+$ antiproter, i.e. they are active ingredients which inhibit the $Na^+/H^+$ exchange mechanism of the cells (Düsing et al., Med. Klin. 1992, 87, 367–384) and are consequently good antiarrhythmic agents which are suitable, in particular, for the treatment of arrhythmia occurring as a consequence of oxygen deficiency.

The substances exhibit a good cardioprotective action and are therefore particularly suitable for the treatment of acute myocardial infarction, infarction prophylaxis, post-infarction treatment, chronic cardiac insufficiency and for the treatment of angina pectoris. They furthermore counter all pathological hypoxic and ischemic damage, enabling the illnesses caused primarily or secondarily thereby to be treated. These active ingredients are likewise highly suitable for preventive applications.

Owing to the protective action of these substances in pathological hypoxic or ischaemic situations, further possible applications arise therefrom in surgical interventions for protection of organs with temporarily reduced supply, in organ transplants for protection of the removed organs, in angioplastic vascular or cardiac interventions, in ischemia of the nervous system, in the therapy of shock states and for the prevention of essential hypertonia.

These compounds can furthermore also be employed as therapeutic agents in illnesses caused by cell proliferation, such as arteriosclerosis, diabetes and late complications of diabetes, tumour illnesses, fibrotic illnesses, in particular of the lungs, liver and kidneys, and organ hypertrophia and hyperplasia. In addition, the compounds are suitable for diagnostic use for the recognition of illnesses accompanied by increased activity of the $Na^+/H^+$ antiporter, for example in erythrocytes, thrombocytes or leukocytes.

The compounds can therefore be used as medicament active ingredients in human and veterinary medicine. They can furthermore be used as intermediates for the preparation of further medicament active ingredients.

The compounds of the formula I can be prepared, for example, as described in EP 0 758 644. The syntheses known hitherto are based on the introduction of alkylsulfone groups into the ring of a corresponding aromatic carboxylic acid and comprise a multiplicity of individual steps, in some cases with unsatisfactory yields. The known processes furthermore have reaction conditions which are disadvantageous for industrial production. Thus, for example, the introduction of alkylsulfone groups into the ring of an aromatic carboxylic acid by nucleophilic substitution of suitable leaving groups with alkylsulfanes followed by oxidation is problematic owing to the extreme and long-lasting odour nuisance by alkylsulfanes, even if they are liberated only in traces.

In the case of direct introduction of the alkylsulfonyl group into the ring of an aromatic carboxylic acid by nucleophilic substitution of suitable leaving groups by means of alkylsulfinate, temperatures of at least 120° C. are necessary, even if highly polar solvents are used, in order to achieve adequate reaction rates. It has been observed that although a slow decomposition reaction occurs in this temperature range, it increases greatly at elevated temperatures with high exothermicity. Owing to the considerable evolution of heat by this decomposition, there is a risk in large batches of the temperature management of the reaction going out of control. It is consequently not possible to use this reaction on an industrial scale for safety reasons.

The object of the present invention was therefore to provide an improved process for the preparation of the compounds of the formula I and their acid-addition salts which circumvents the above-mentioned problematic reaction steps and in addition provides better yields.

This object has been achieved by the process according to the invention having the features described herein. It has been found, surprisingly, that the exchange of the leaving group X in the esters of the formula III proceeds significantly more quickly or at lower temperature than in the case of the corresponding free acid which is employed in the processes of the prior art, resulting in a considerable improvement in yield. The process according to the invention therefore also enables inexpensive starting compounds with chlorine substituents on the aromatic ring as leaving groups to be used with very good results. It has furthermore been found that, in accordance with the process according to the invention, it is possible to carry out steps A and B and steps C and D one after the other without working up the reaction mixtures, enabling losses of yield and complex working steps to be avoided.

In the compounds of the formulae I, II, III and IV, the radicals have the following preferred meanings:

$R^1$, $R^2$, $R^3$ and $R^4$ are, independently, preferably methyl, ethyl, n-propyl, n-butyl or n-pentyl. Particular preference is given to methyl or ethyl, in particular methyl.

X is preferably F, $CF_3SO_2$ or Cl, in particular Cl.

The process according to the invention is particularly suitable for the preparation of acid-addition salts of compounds of the formula I in which $R^1$, $R^2$ and $R^3$ are simultaneously a methyl group (compounds of the formula IA). A very particularly preferred acid-addition salt is the hydrochloride.

The process is therefore particularly suitable for the preparation of the compound of the formula V:

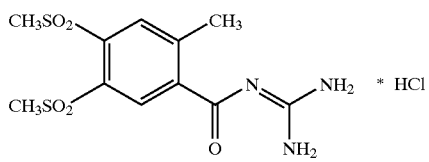

V

The reaction in the process according to the invention is simple to carry out, the relevant starting compounds of the formula II being converted, in step A, into the corresponding esters by the conventional esterification methods known from the literature, such as, for example, acid-catalysed esterification using a corresponding alcohol, such as methanol or ethanol, in the presence of excess alcohol as solvent or in the presence of a suitable cosolvent, reaction of the carboxylic acid salts of compounds of the formula II with a suitable alkylating agent, such as, for example, dialkyl sulfate, or reaction of the free acids with orthoesters.

A further possible esterification reaction is conversion of the acid into an acid halide and subsequent reaction with a corresponding alcohol to give the ester.

The esterification is preferably carried out by reaction of the carboxylic acid salts of compounds of the formula II with alkylating agents, such as, for example, dialkyl sulfate, or reaction of the compounds of the formula II with an orthoester.

The reaction of the carboxylic acid salts with alkylating agents is advantageously carried out by preferably adding a dialkyl sulfate to the respective carboxylic acid salt dissolved in an inert solvent, the salt preferably being prepared in situ by addition of a base, such as, for example, alkali metal carbonate, hydrogencarbonate, hydroxide or alkoxide, in particular an alkoxide, such as, for example, potassium tert-butoxide, or a hydroxide, such as, for example, sodium hydroxide, and reacting the reactants at room temperature or elevated temperature and atmospheric pressure. Dimethyl sulfate and diethyl sulfate are particularly preferred as alkylating agents.

The carboxylic acid of the formula II to be esterified, or the salt thereof, is preferably employed in a molar ratio to the alkylating agent of from 1:1 to 1:8, in particular from 1:2 to 1:4.

The esterification is particularly preferably achieved by reacting the corresponding acids with an orthoester, such as, for example, trialkyl orthoacetate, tetraalkyl orthocarbonate or orthosilicate. Preferred orthoesters are trimethyl or triethyl orthoacetate, tetramethyl or tetraethyl orthocarbonate or orthosilicate. Tetramethyl orthoacetate is particularly preferred. The esterification reaction is advantageously reacted at elevated temperatures, preferably at 30–180° C., in particular at 80–120° C., in an inert solvent.

The carboxylic acid of the formula II to be esterified is preferably employed in a molar ratio to the orthoester of from 1:1 to 1:5, in particular from 1:1.5 to 1:3.

Preferred inert solvents for step A are amides, such as, for example, dimethylformamide, dimethylacetamide, tetramethylurea, cyclic ureas, such as, for example, N,N-dimethylimidazolidinone, or hexamethylphosphoric triamide or 1-methyl-2-pyrrolidone (N-methylpyrrolidone, NMP). If the esterification is carried out by means of an orthoester, preference is furthermore given to ethers, such as, for example, diethyl ether, tetrahydrofuran or dioxane, or hydrocarbons, such as, for example, toluene, benzene, hexane or heptane. NMP is particularly preferred.

Mixtures of the said solvents can likewise be used.

The duration of the reaction in step A depends on the reaction conditions selected. In general, the reaction duration is from 0.5 hours to 2 days, preferably from 1 to 15 hours.

In step B, the compounds of the formula III are reacted with alkylsulfinate, preferably with alkali metal alkylsulfinate, preferably in polar aprotic solvents at temperatures which are preferably in the range 30–150° C., preferably 50–110° C., in particular at 80–90° C.

The alkali metal alkylsulfinate used is preferably sodium alkylsulfinate or potassium alkylsulfinate, in particular sodium methylsulfinate or potassium methylsulfinate.

The compounds of the formula III are preferably employed in a molar ratio to the alkali metal alkylsulfinate of from 1:1 to 1:4, in particular from 1:1.5 to 1:3.

Suitable polar aprotic solvents for step B are preferably dimethyl sulfoxide, sulfolane (tetrahydrothiophene 1,1-dioxide), dimethylformamide, dimethylacetamide, tetramethylurea, cyclic ureas, such as, for example, N,N-dimethylimidazolidinone, or hexamethylphosphoric triamide or N-methyl-pyrrolidone (NMP). NMP is particularly preferred.

Mixtures of the said solvents can likewise be used.

The duration of the reaction in step B depends on the reaction conditions selected. In general, the reaction duration is from 0.5 hours to 2 days, preferably from 1 to 25 hours.

In a particularly preferred embodiment of the invention, step B can be carried out without work-up of the reaction mixture after step A. To this end, the esterification of the compounds of the formula II is carried out as described above by reaction with alkylating agents or preferably by reaction with orthoesters in a polar aprotic solvent which can also be used for step B, preferably NMP. Alkylsulfinate is subsequently added to the resultant reaction mixture, and the mixture is allowed to react further in the manner described above for step B.

In step C, the compounds of the formula IV are reacted with guanidine, preferably in an organic solvent at temperatures of from −20 to +60° C., preferably at from −10 to +30°, at atmospheric pressure. The organic solvents used for this step are preferably ethers, such as tetrahydrofuran or dioxane, or alcohols, such as methanol, ethanol, n-propanol or i-propanol. Mixtures of the said solvents can likewise be used. In a preferred embodiment of the invention, the guanidine is liberated from its acid-addition salt, such as, for example, the guanidinium chloride, in one of these solvents by addition of a base, such as, for example, alkali metal hydroxide oralkoxide, in particular sodium methoxide, and subsequently reacted without with the compounds of the formula IV.

The compounds of the formula IV are preferably employed in a molar ratio to the guanidine of from 1:1 to 1:6, in particular from 1:2 to 1:4.

The duration of the reaction in step C depends on the reaction conditions selected. In general, the reaction duration is from 0.5 hours to 20 hours, preferably from 1 to 5 hours.

In step D, the acid-addition salt is formed by treatment of the compounds of the formula I with a corresponding acid. Suitable acids are preferably those which form physiologically acceptable and tolerated salts with the compounds of the formula I.

Use can preferably be made for this purpose of inorganic acids, for example sulfuric acid, nitric acid, hydrohalic acids, such as hydrochloric acid or hydrobromic acid, phosphoric acids, such as orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, or laurylsulfuric acid. Hydrochloric acid is particularly preferred.

The treatment with an acid is preferably carried out by dissolving the compounds of the formula I in a solvent and adding an equimolar amount of the gaseous or liquid acid or a solution of the acid in a suitable solvent.

In a preferred embodiment of the invention, step D can be carried out after step C without prior work-up of the reaction mixture, i.e. without isolation of the compound of the formula I, where, in order to form the acid-addition salt, the corresponding acid is added directly to the reaction mixture obtained from step C. In this case, the acid-addition salt of the compounds of the formula I precipitates from the solution in crystalline form.

The amounts of solvents for the individual steps A, B, C and D is not crucial, it preferably being possible to add from 10 g to 500 g of solvent per g of the compounds of the formulae I, II, III or IV to be reacted.

The compounds of the formulae I, II, III and IV can be obtained by conventional work-up steps, such as, for example, addition of water to the reaction mixture and extraction after removal of the solvent. It may be advantageous to follow this by a distillation or crystallisation for further purification of the product.

Even without further embodiments, it is assumed that a person skilled in the art will be able to use the above description in the broadest scope. The preferred embodiments are therefore merely to be regarded as descriptive disclosure which is in no way limiting in any manner.

The examples below are intended to illustrate the invention without representing a limitation. Unless stated otherwise, percentages denote percent by weight. All temperatures are given in degrees Celsius.

The following abbreviations are used:

| THF | tetrtahydrofuran |
| KOtBu | potassium tert-butoxide |
| RT | room temperature |
| MTBE | methyl tert-butyl ether |
| h | hour(s) |
| d | day(s) |

EXAMPLE 1

A solution of 29.5 g of 4-chloro-5-methanesulfonyl-2-methylbenzoic acid and 18.39 g of trimethyl orthoacetate in 100 ml of dioxane was refluxed until the acid had reacted completely. 150 ml of toluene were added, and the solvent was removed to the extent that the mixture still remained stirrable. 150 ml of 1-methyl-2-pyrrolidone (NMP) and 15.8 g of sodium methanesulfinate were subsequently added, and the mixture was stirred at 80° C. for 5 h. After addition of a further 5.3 g of sodium methanesulfinate, the mixture was stirred for 25 h. Conventional work-up gave methyl 4,5-bismethanesulfonyl-2-methylbenzoate.

EXAMPLE 2

A solution of 100.0 g of 4-chloro-5-methanesulfonyl-2-methylbenzoic acid and 68.1 g of trimethyl orthoacetate in 322 ml of NMP was refluxed until the acid had reacted completely. After the excess orthoester had been distilled off, 96.5 g of sodium methanesulfinate were added, and the mixture was stirred at 90° C. for 18 h. Conventional work-up gave methyl 4,5-bis-methanesulfonyl-2-methylbenzoate.

EXAMPLE 3

87.4 ml of THF, were added with stirring to 50.4 g of a 30% sodium methoxide solution in methanol. 28.95 g of guanidinium chloride were subsequently introduced. The suspension was stirred at 16–24° C. for 2 h and cooled to 10° C., before 30.8 g of methyl 4,5-bismethanesulfonyl-2-methylbenzoate were introduced into the mixture. After the mixture had been stirred at 10° C. for 1 h, a corresponding amount of a hydrochloric acid solution was added to the mixture. Conventional work-up gave N-(4,5-bis-methanesulfonyl-2-methylbenzoyl)guanidinium chloride.

What is claimed is:

1. A process for preparing an acid-addition salt of a compound of the formula I

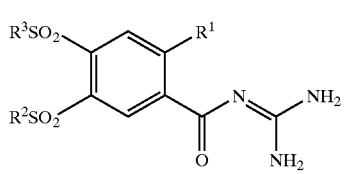

in which $R^1$, $R^2$ and $R^3$, independently of one another, are alkyl having from 1 to 12 carbon atoms, comprising a) converting a compound of formula II

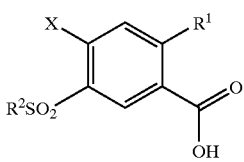

in which R¹ and R² are as defined above, and X is F, Cl, Br, alkyl- or arylsulfonate or perfluoroalkylsulfonate, into an ester of the formula III

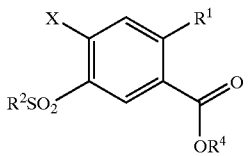

in which R¹, R² and X are as defined above, and R⁴ is alkyl having from 1 to 10 carbon atoms,
b) converting a compound of formula III in the presence of alkylsulfinate into a compound of formula IV

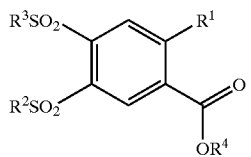

in which R¹, R², R³ and R⁴ are as defined above, compounds of the formula converted by
c) reacting a compound of formula IV with guanidine to form a compound of formula I, and,
d) treating a compound of formula I with an acid in order to form an acid-addition salt.

2. A process according to claim 1, wherein b) is carried out after a) without work-up of the resultant reaction mixture of a).

3. A process according to claim 1, wherein d) is carried out after c) without work-up of the resultant reaction mixture of c).

4. A process according to claim 1, wherein X in formula II is Cl.

5. A process according to claim 1, step A, wherein a) comprises reacting a compound of formula II with an orthoester.

6. A process according to claim 1, wherein a) and b) are carried out in the presence of 1-methyl-2-pyrrolidone steps A and B.

7. A process according to claim 1, wherein b) is carried out at a temperature of 50–110° C.

8. A process according to claim 1, wherein the acid used in d) is hydrochloric acid.

9. A process according to claim 1, wherein an acid-solution salt of the compound of formula IA is obtained

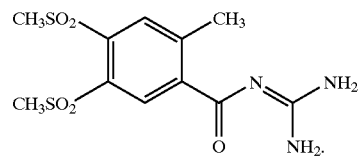

10. A process according to claim 1 wherein the acid-addition salt of formula V is obtained

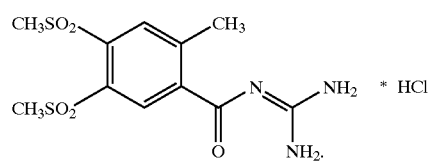

11. A process according to claim 1, wherein R¹, R², R³ and R⁴ are, each independently, methyl ethyl, n-propyl, n-butyl or n-pentyl.

12. A process according to claim 1, wherein X is F, CF₃SO₂ Cl.

13. A process according to claim 1, wherein R¹, R² and R³ are each methyl.

14. A process according to claim 1, wherein the acid-addition salt of a compound of formula I is a hydrochloride salt of a compound of formula I.

15. A process according to claim 1, wherein the quanidine in c) is obtained from an acid-addition salt of quanidine.

16. A process according to claim 1, wherein the acid-addition salt of a compound of formula I is a physiologically acceptable acid-addition salt.

17. A process according to claim 1, further comprising bringing together an acid-addition salt of a compound of formula I and a physiologically acceptable carrier.

* * * * *